(12) United States Patent
Kim et al.

(10) Patent No.: US 10,031,055 B2
(45) Date of Patent: Jul. 24, 2018

(54) TENSILE TEST PIECE AND METHOD FOR MANUFACTURING THE SAME

(71) Applicants: Samsung Display Co., Ltd., Yongin-si, Gyeonggi-do (KR); UNIST (ULSAN NATIONAL INSTITUTE OF SCIENCE AND TECHNOLOGY), Ulsan (KR)

(72) Inventors: Young Chan Kim, Incheon (KR); Won Sang Park, Yongin-si (KR); Hye Yong Chu, Hwaseong-si (KR); Jong Ho Hong, Yongin-si (KR); Si-Hoon Kim, Ulsan (KR); Ju-Young Kim, Ulsan (KR); Yun Seok Nam, Ulsan (KR); Myoung Hoon Song, Ulsan (KR)

(73) Assignees: Samsung Display Co., Ltd., Yongin-si (KR); UNIST(Ulsan National Institute of Science and Technology), Ulju-Gun, Ulsan (KR)

( * ) Notice: Subject to any disclaimer, the term of this patent is extended or adjusted under 35 U.S.C. 154(b) by 0 days.

(21) Appl. No.: 15/238,685

(22) Filed: Aug. 16, 2016

(65) Prior Publication Data
US 2017/0074761 A1    Mar. 16, 2017

(30) Foreign Application Priority Data
Sep. 14, 2015 (KR) .................. 10-2015-0129963

(51) Int. Cl.
*G01N 3/08* (2006.01)
*G01N 3/06* (2006.01)

(52) U.S. Cl.
CPC .............. *G01N 3/08* (2013.01); *G01N 3/06* (2013.01)

(58) Field of Classification Search
CPC ................................. G01N 3/08; G01N 3/06
(Continued)

(56) References Cited

U.S. PATENT DOCUMENTS 4,895,750 A * 1/1990 Pratt .................. C04B 41/009
  428/137
5,085,083 A * 2/1992 Corr .................... G01N 3/02
  73/760

(Continued)

FOREIGN PATENT DOCUMENTS

KR    104999-005522 A    7/1999
KR    10-0665517 B1       1/2007
(Continued)

OTHER PUBLICATIONS

Fan et al. "Performance investigation of organic photovoltaic layers on architectural membrane". Advanced Building Skins, Conference Proceedings of the 9th Energy Forum, Oct. 28-29, 2014. <https://www.researchgate.net/publication/276274477_Performance_investigation_of_organic_photovoltaic_layers_on_architect ural membrane>.*

(Continued)

Primary Examiner — Jonathan Dunlap
(74) Attorney, Agent, or Firm — Lewis Roca Rothgerber Christie LLP

(57) ABSTRACT

A method for manufacturing a tensile test piece according to one or more exemplary embodiments includes: preparing a polymer layer including a non-conductive material; forming a sacrificial layer on the polymer layer; forming a planarization layer on the sacrificial layer; shaping the polymer layer, the sacrificial layer, and the planarization layer into a dog-bone-shaped sample; etching at least a portion of the sample; and drying the sample.

13 Claims, 24 Drawing Sheets

(58) Field of Classification Search
USPC .......................................... 73/826, 856, 760
See application file for complete search history.

(56) References Cited

U.S. PATENT DOCUMENTS

| | | | |
|---|---|---|---|
| 6,422,528 B1* | 7/2002 | Domeier | B29C 33/3857 |
| | | | 249/135 |
| 7,798,014 B2* | 9/2010 | Ferguson | G01N 3/08 |
| | | | 73/831 |
| 7,854,173 B2* | 12/2010 | Cheng | G01B 7/18 |
| | | | 73/760 |
| 7,878,071 B2 | 2/2011 | Greer | |
| 2007/0209447 A1* | 9/2007 | Christ, Jr. | G01L 1/247 |
| | | | 73/800 |
| 2016/0169783 A1* | 6/2016 | Levasseur | G01B 7/16 |
| | | | 73/826 |

FOREIGN PATENT DOCUMENTS

| | | |
|---|---|---|
| KR | 10-2013-0134710 | 12/2013 |
| KR | 10-2013613471 | 5/2014 |

OTHER PUBLICATIONS

Lang et al,, Microtensile testing of submicrometer thick functional polymer samples, Review of Scientific Instruments, 83, 075110 , Jul. 19, 2012, 6 pages.

Lang et al., Mechanical characterization of PEDOT:PSS -thin films, Synthetic Metals 159 (2009), pp. 473-479, 7 pages.

* cited by examiner

TENSILE TEST PIECE AND METHOD FOR MANUFACTURING THE SAME

CROSS-REFERENCE TO RELATED APPLICATION

This application claims priority to and the benefit of Korean Patent Application No. 10-2015-0129963, filed in the Korean Intellectual Property Office on Sep. 14, 2015, the entire contents of which are incorporated herein by reference.

BACKGROUND

1. Field

The present disclosure relates to a tensile test piece and a method for manufacturing the same.

2. Description of the Related Art

Currently known flat panel displays include liquid crystal displays (LCDs), plasma display panels (PDPs), organic light emitting diode (OLED) displays, field effect displays (FEDs), electrophoretic displays, and the like.

Displays, mobile phones, digital gadgets, and information technology (IT) devices in which display elements and memory elements are constructed on a flexible substrate to provide improved portability and mobility have been recently developed. In addition, because industries and markets for transparent displays have recently expanded, transparent, conductive, and flexible substrates and materials for the transparent displays are being actively developed. To evaluate physical properties of a flexible substrate and a flexible material, such as extension and the like, a tensile test piece formed with a gauge having a middle part with a relatively small width is generally prepared and mounted on the flexible material, and is extended to measure a change of the tensile test piece.

To manufacture such a tensile test piece, a poly(3,4-ethylenedioxythiophene) polystyrene sulfonate (PEDOT:PSS) layer is coated on a substrate, and the substrate is air-dried and then laser-cut. However, when performing the laser-cutting, a gauge part of the tensile sample may be non-uniformly formed due to degradation caused by the laser, and therefore various properties may not be correctly evaluated when the tensile test piece is applied.

In addition, tensile test pieces with varying thicknesses should be provided depending on a size of the flexible material.

The above information disclosed in this Background section is only to enhance the understanding of the background of the described technology and therefore it may contain information that does not form prior art.

SUMMARY

Exemplary embodiments of the present invention provide a method for manufacturing a customizable tensile test piece having a uniform shape and having a thickness according to a size of a flexible material.

A method for manufacturing a tensile test piece according to one or more exemplary embodiments includes: preparing a polymer layer including a non-conductive material; forming a sacrificial layer on the polymer layer; forming a planarization layer on the sacrificial layer; shaping the polymer layer, the sacrificial layer, and the planarization layer into a dog-bone-shaped sample; etching at least a portion of the sample; and drying the sample.

The method for manufacturing a tensile test piece according to one or more exemplary embodiments may further include forming a copper layer on the polymer layer.

The forming of the sacrificial layer and the forming of the planarization layer may include a spin coating method.

The shaping the polymer layer, the sacrificial layer, and the planarization layer into the sample may include a press cutting method.

A length of a gauge of a middle part of the sample may be greater than or equal to 4 mm and less than or equal to 6 mm.

A total thickness of the sample may be greater than or equal to 500 nm and less than or equal to 600 nm.

The drying the sample may include attaching the sample to an auxiliary guide and air-drying the sample.

The shaping the polymer layer, the sacrificial layer, and the planarization layer into the sample may include a reactive ion etching (RIE) process utilizing a dog-bone-shaped hard mask.

A length of a gauge of a middle part of the sample may be greater than or equal to 1 mm and less than or equal to 2 mm.

A total thickness of the sample may be greater than or equal to 100 nm and less than or equal to 100 μm.

The shaping the polymer layer, the sacrificial layer, and the planarization layer into the sample may include a reactive ion etching (RIE) process after performing a photolithography process utilizing a dog-bone-shaped hard mask.

A length of a gauge of a middle part of the sample may be greater than or equal to 250 μm and less than or equal to 300 μm.

A total thickness of the sample may be greater than or equal to 10 nm and less than or equal to 10 μm.

A tensile test piece according to one or more exemplary embodiments includes: a polymer layer including a non-conductive material; a sacrificial layer on the polymer layer; a planarization layer on the sacrificial layer; wherein a lamination of the polymer layer, the sacrificial layer, and the planarization layer is dog-bone-shaped.

The polymer layer may include at least one of polyimide (PI), polyethylene terephthalate (PET), polyethersulfone (PES), polyethylene naphthalate (PEN), polycarbonate (PC), polymethyl methacrylate (PMMA), polyvinyl alcohol (PVA), triacetyl cellulose (TAC), polystyrene (PS), polyether imide (PEI), polydimethylsiloxane (PDMS), a silicone resin, a fluorine resin, and a modified epoxy resin.

The sacrificial layer may include polymethyl methacrylate (PMMA).

The planarization layer may include poly(3,4-ethylenedioxythiophene) polystyrene sulfonate (PEDOT:PSS).

According to one or more exemplary embodiments, a tensile test piece can be manufactured to have a uniform shape, and the flexible display can be manufactured such that the tensile test piece for evaluating physical properties of the flexible material, such as extension and the like, is customized to have a different thickness relative to a size of the flexible material to be tested.

DETAILED DESCRIPTION

Figure 1:
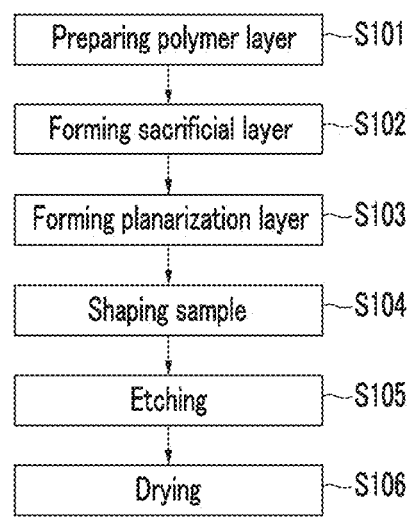
FIG. 1 is a flowchart illustrating a method for manufacturing a tensile test piece according to one or more exemplary embodiments.

Exemplary embodiments of the present invention are described more fully hereinafter with reference to the accompanying drawings, in which like reference numbers refer to like elements throughout. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. As those skilled in the art would realize, the described embodiments may be modified in various different ways, all without departing from the spirit or scope of the present invention. In the drawings, the relative sizes of elements, layers, and regions may be exaggerated for clarity.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration. In addition, the use of alternative language, such as "or," when describing embodiments of the present invention, refers to "one or more embodiments of the present invention" for each corresponding item listed. When a part is referred to as being "on" another part, it can be directly on the other part or intervening parts may also be present.

Also, any numerical range disclosed and/or recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a) and 35 U.S.C. § 132(a).

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

A method for manufacturing a tensile test piece according to one or more exemplary embodiments is described below with reference to FIG. 1 and FIGS. 2A to 2G.

FIG. 1 is a flowchart illustrating a method for manufacturing a tensile test piece according to one or more exemplary embodiments, and FIGS. 2A to 2G are processing diagrams illustrating the method for manufacturing a tensile test piece according to one or more exemplary embodiments.

Figure 2A:
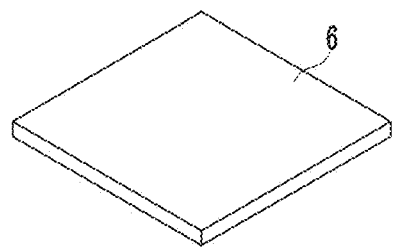
FIGS. 2A-2G are processing diagrams illustrating a method for manufacturing a tensile test piece according to one or more exemplary embodiments.
Figure 2B:
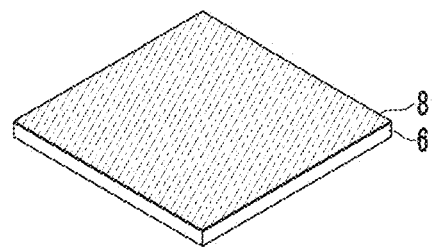

First, referring to FIG. 1 and FIGS. 2A to 2G, a polymer layer 6 including a non-conductive material is prepared (S101) (see, for example, FIG. 2A). The polymer layer 6 is a curable polymer that can be utilized as a substrate material, and does not have a conductive property. In some exemplary embodiments, the polymer layer 6 may be formed of polypropylene. A copper layer 8 may be formed on the polymer layer 6 (see, for example, FIG. 2B).

Figure 2C:
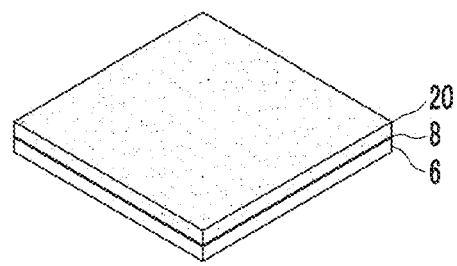

Next, a sacrificial layer 20 is formed on the polymer layer 6 (e.g., on the copper layer 8) (S102) (see, for example, FIG. 2C). The sacrificial layer 20 may include an organic material, and may be formed of a hydrophobic material, such as polymethylmethacrylate (PMMA), a photosensitive polymer (PR), and/or polyvinyl phenol (PVP). Before forming the sacrificial layer (S102), a cleaning step for removing impurities on the surface of the polymer layer 6 and/or the copper layer 8 to effectively form the sacrificial layer 20 may be performed. In addition, after forming the sacrificial layer 20, a drying or curing process may be performed.

Figure 2D:
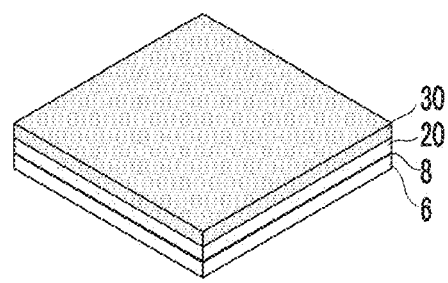

Next, a planarization layer 30 is formed on the sacrificial layer 20 (S103) (see, for example, FIG. 2D). The planarization layer 30 may include a conductive material and a surfactant, and has a conductive property. For example, the planarization layer 30 may include a conductive material such as poly(3,4-ethylenedioxythiophene) polystyrene sulfonate (PEDOT:PSS), and may include a surfactant, such as a fluorine-based surfactant.

The sacrificial layer 20 (S102) and the planarization layer 30 (S103) may be formed by a spin coating method, for example. In addition, the sacrificial layer 20 and the planarization layer 30 may be formed by bar coating, slit coating, roll coating, and/or off-set coating methods, for example.

Figure 2E:
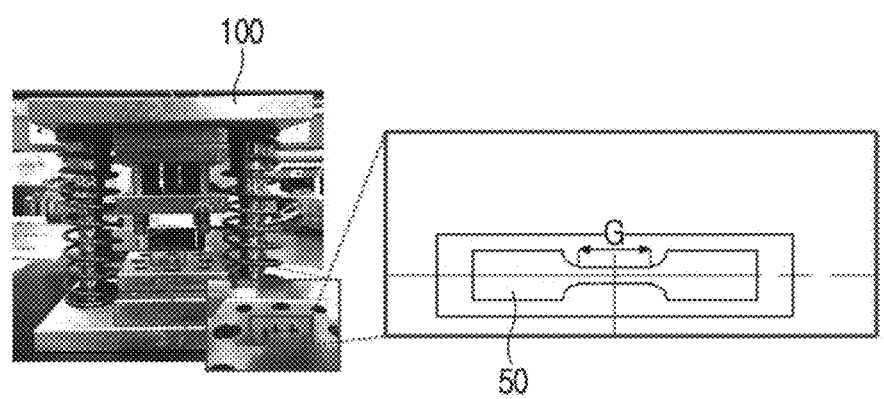

Next, a lamination of the polymer layer 6, the copper layer 8, the sacrificial layer 20, and the planarization layer 30 is shaped into a sample (e.g., a dog-bone-shaped sample) 50 (S104) (see, for example, FIG. 2E). For example, the sample 50 may be shaped by a press cutting method. A suitable dog-bone-shaped opening is formed in a press lathe 100 that is used for press cutting, and the lamination of the polymer layer 6, the copper layer 8, the sacrificial layer 20, and the planarization layer 30 is placed on the press lathe 100, and then pressed and cut by a high-hardness cutting tool, thereby forming the dog-bone-shaped sample 50.

A length of a gauge G of a middle part of the sample 50 (see, for example, FIG. 2E) may be formed to have a length that is greater than or equal to about 4 mm and less than or equal to about 6 mm (e.g., a length in a first direction). In addition, a total thickness of the sample 50 may be formed to be greater than or equal to about 500 nm and less than or equal to about 600 nm (e.g., a thickness in a second direction).

Figure 2F:
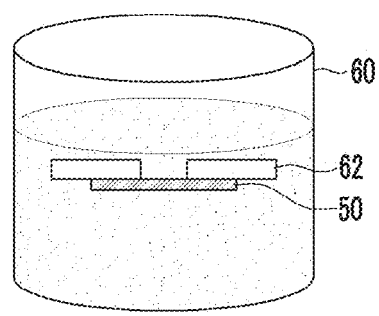

Next, the sample 50 is etched (e.g., selectively etched) (S105) (see, for example, FIG. 2F). An etching solution is provided in an etching container 60 having a stand 62 therein, and the sample 50 is placed on the stand 62 and is then selectively etched. Acetone may be used as the etching solution, for example. While etching the sample (S105), a protruding part that is non-uniformly formed in the sample 50 may be removed or smoothed by etching.

Figure 2G:
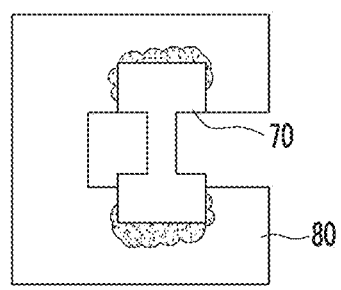

Next, the etched sample 50 is dried (S106) (see, for example, FIG. 2G). The sample 50 is removed from the etching solution and attached to an auxiliary guide 80 and then air-dried to manufacture a tensile test piece 70. Any etching solution remaining on an external surface of the sample 50 may be removed by a drying process (S106).

FIGS. 3A to 3G are processing diagrams illustrating a method for manufacturing a tensile test piece according to one or more exemplary embodiments. Referring to FIGS. 3A to 3G, preparation of a polymer layer 10 including a non-conductive material (see, for example, FIG. 3A), formation of a sacrificial layer 20 on the polymer layer 10 (see, for example, FIG. 3B), and formation of a planarization layer 30 on the sacrificial layer 20 (see, for example, FIG. 3C) are the same or substantially the same as in the exemplary embodiment described above with respect to FIGS. 2A to 2C.

A sample 50 (see, for example, FIG. 3D) according to one or more embodiments of the present invention may be shaped by a reactive ion etching (RIE) process utilizing a hard mask (e.g., a dog-bone-shaped hard mask) M. The reactive ion etching method, which is a dry etching method, enables high precision processing by performing anisotropy etching in which the dog-bone-shaped hard mask M is placed on the formed lamination of the polymer layer 10, the sacrificial layer 20, and the planarization layer 30 and supplying an active gas in a plasma state thereto, thereby vertically etching a part of the lamination which is not covered by the hard mask M.

A length of a gauge G of the sample 50 (see, for example, FIG. 3E) may be greater than or equal to about 1 mm and less than or equal to about 2 mm (e.g., a length in a first direction). In addition, a total thickness of the sample 50 may be greater than or equal to about 100 nm and less than or equal to about 100 μm (e.g., a thickness in a second direction).

Figure 3A:
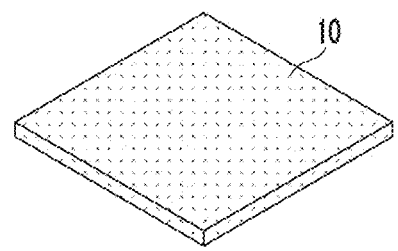
FIGS. 3A-3G are processing diagrams illustrating a method for manufacturing a tensile test piece according to one or more exemplary embodiments.
Figure 3B:
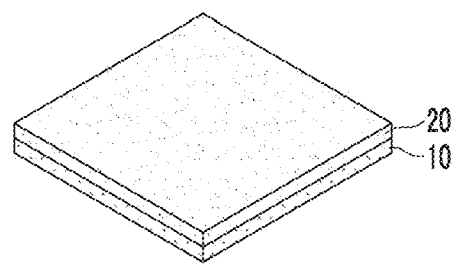
Figure 3C:
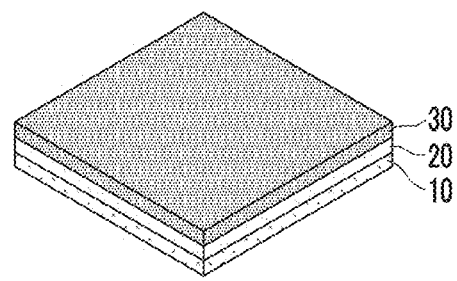
Figure 3D:
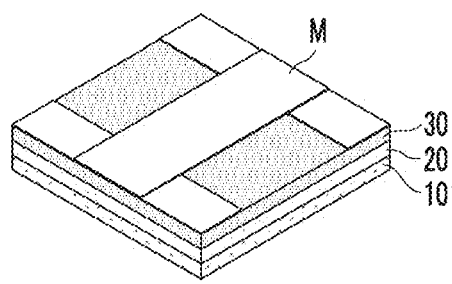
Figure 3E:
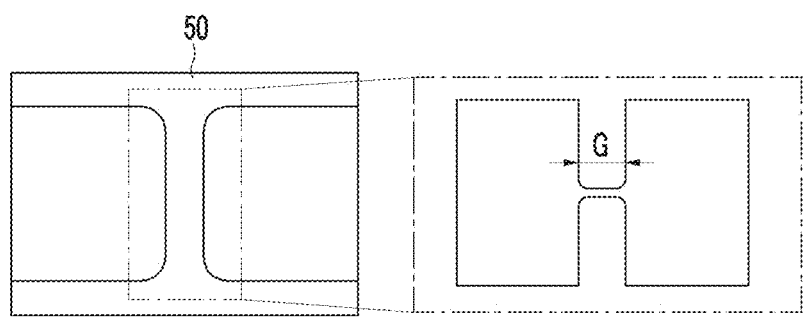
Figure 3F:
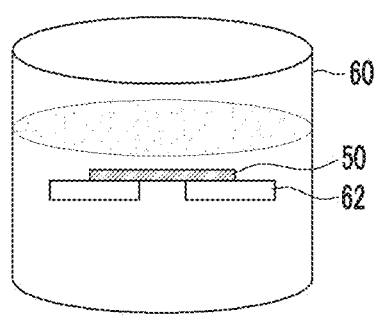
Figure 3G:
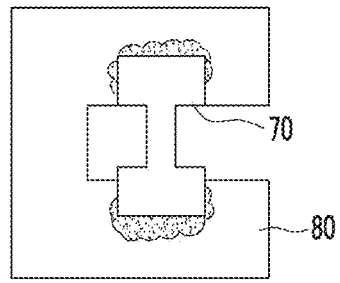

Next, the sample 50 is selectively etched utilizing an acetone solution (see, for example, FIG. 3F). The etched sample 50 is attached to an auxiliary guide 80 and then air-dried (see, for example, FIG. 3G) to form a tensile test piece 70, similar to the tensile test piece according to one or more exemplary embodiments described above with reference to FIGS. 2F and 2G.

FIGS. 4A to 4H are processing diagrams illustrating a method for manufacturing a tensile test piece according to one or more exemplary embodiments. Referring to FIGS. 4A to 4H, preparation of a polymer layer 10 including a non-conductive material (see, for example, FIG. 4A), formation of a sacrificial layer 20 on the polymer layer 10 (see, for example, FIG. 4B), and formation of a planarization layer 30 on the sacrificial layer 20 (see, for example, FIG. 4C) are the same or substantially the same as in the exemplary embodiment described above with respect to FIGS. 2A to 2C.

A sample 50 according to one or more embodiments of the present invention may be shaped by a reactive ion etching process after performing a photolithography process utilizing a hard mask (e.g., a dog-bone-shaped hard mask) M.

Figure 4A:
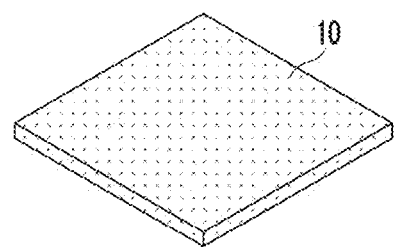
FIGS. 4A-4H are processing diagrams illustrating a method for manufacturing a tensile test piece according to one or more exemplary embodiments.
Figure 4B:
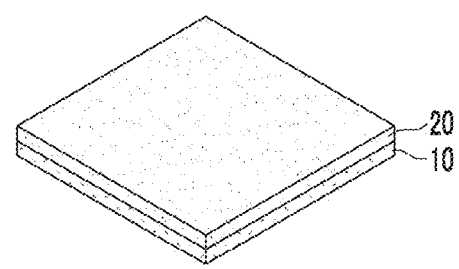
Figure 4C:
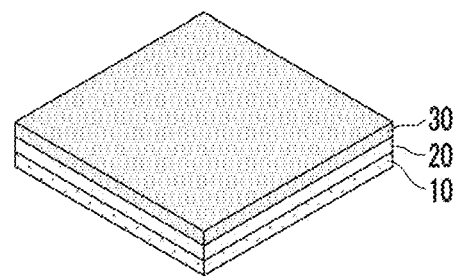
Figure 4D:
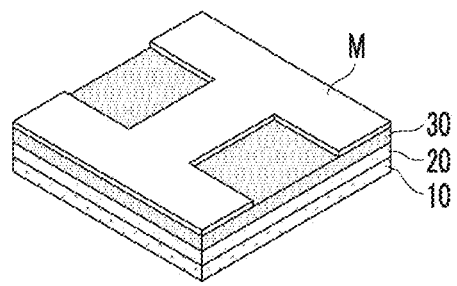
Figure 4E:
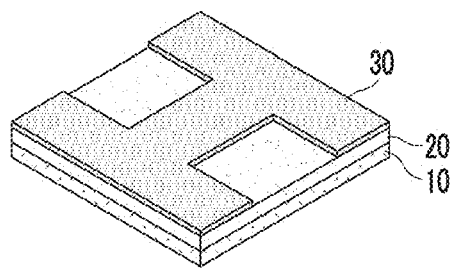
Figure 4F:
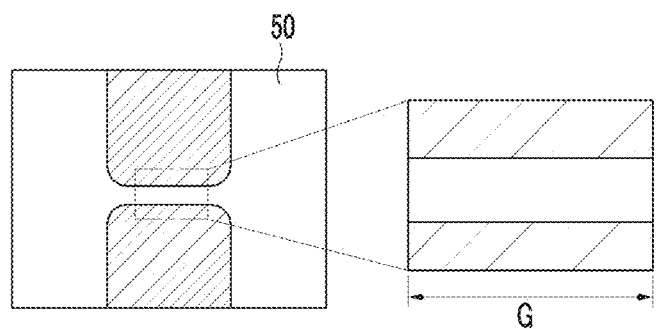
Figure 4G:
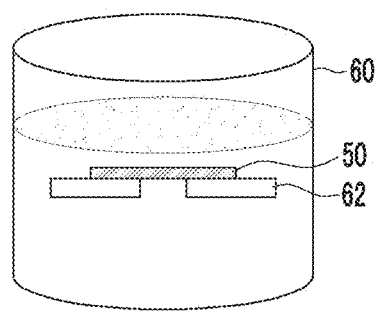
Figure 4H:
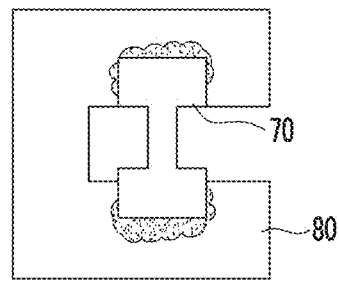

After a photosensitive photoresist is thinly coated on the lamination of the polymer layer 10, the sacrificial layer 20, and the planarization layer 30, the dog-bone-shaped hard mask M is disposed thereon (see, for example, FIG. 4D). An exposed portion of the planarization layer 30 is removed via development (see, for example, FIG. 4E). Next, an active gas in a plasma state is supplied to the lamination, and the sacrificial layer 20 and the polymer layer 10 are reactive ion etched such that they have the same or substantially the same shape as the planarization layer 30 (see, for example, FIG. 4F).

A length of a gauge of the sample 50 (see, for example, FIG. 4F) may be greater than or equal to about 250 μm and less than or equal to about 300 μm. In addition, a total thickness of the sample 50 may be formed to be greater than or equal to about 10 nm and less than or equal to about 10 μm.

To manufacture a tensile test piece 70, the sample 50 is then selectively etched utilizing an acetone solution (see, for example, FIG. 4G), attached to an auxiliary guide 80, and air-dried (see, for example, FIG. 4H), as described above with reference to FIGS. 2F and 2G.

Figure 5:
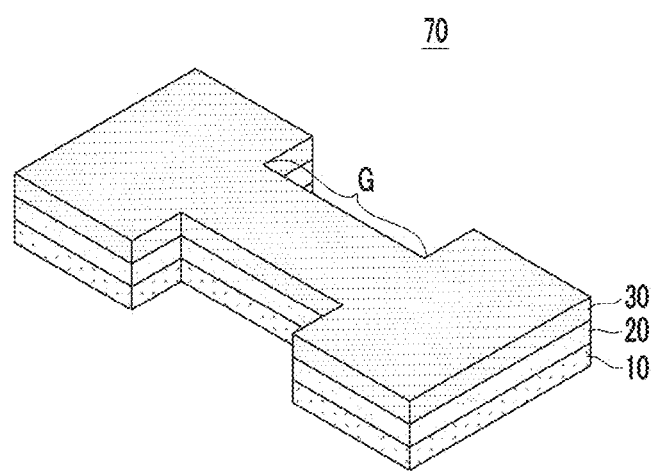
FIG. 5 is a schematic perspective view illustrating a tensile test piece according to one or more exemplary embodiments.

FIG. 5 is a schematic perspective view of a tensile test piece according to one or more exemplary embodiments. Referring to FIG. 5, a tensile test piece 70 includes a polymer layer 10 including a non-conductive material, a sacrificial layer 20 formed on the polymer layer 10, and a planarization layer 30 formed on the sacrificial layer 20. A lamination of the polymer layer 10, the sacrificial layer 20, and the planarization layer 30 is dog-bone-shaped.

The polymer layer 10 may include at least one of polyimide (PI), polyethylene terephthalate (PET), polyethersulfone (PES), polyethylene naphthalate (PEN), polycarbonate (PC), polymethyl methacrylate (PMMA), polyvinyl alcohol (PVA), triacetyl cellulose (TAC), polystyrene (PS), polyether imide (PEI), polydimethylsiloxane (PDMS), a silicone resin, a fluorine resin, and a modified epoxy resin. A copper layer may be further included on the polymer layer 10.

The sacrificial layer 20 may include an organic material and may be formed of a hydrophobic material, such as polymethylmethacrylate (PMMA), a photosensitive polymer (PR), and/or polyvinyl phenol (PVP), and the planarization layer 30 may include, for example, poly(3,4-ethylenedioxythiophene) polystyrene sulfonate (PEDOT:PSS).

A length of a gauge G of a middle part of the tensile test piece 70 may be formed to be greater than or equal to about 4 mm and less than or equal to about 6 mm (e.g., a length in a first direction), and a total thickness of the tensile test piece 70 may be formed to be greater than or equal to about 500 nm and less than or equal to about 600 nm (e.g., a thickness in a second direction). In addition, the length of the gauge G of the middle part of the tensile test piece 70 may be formed to be greater than or equal to about 1 mm and less than or equal to about 2 mm, and the total thickness of the tensile test piece 70 may be formed to be greater than or equal to about 100 nm and less than or equal to about 100 μm. Alternatively, the length of the gauge G of the middle part of the tensile test piece 70 may be formed to be greater than or equal to about 250 μm and less than or equal to about 300 μm, and the total thickness of the tensile test piece 70 may be formed to be greater than or equal to about 10 nm and less than or equal to 10 μm.

As such, in accordance with the tensile test piece according to one or more exemplary embodiments and the manufacturing method thereof, the tensile test piece can be manufactured such that it has a uniform shape, and such that the tensile test piece for evaluating physical properties of the flexible material, such as extension and the like, is customizable to have a different thickness depending on a size of the material to be tested.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims and their equivalents.

| Description of Some of the Symbols | |
|---|---|
| 6, 10: polymer layer | 8: copper layer |
| 20: sacrificial layer | 30: planarization layer |
| 50: sample | 60: etching container |
| 70: tensile test piece | 80: auxiliary guide |
| 100: press lathe | G: gauge |
| M: mask | |

What is claimed is:

1. A method for manufacturing a tensile test piece, the method comprising:
    preparing a polymer layer comprising a non-conductive material;
    forming a sacrificial layer on the polymer layer;
    forming a planarization layer on the sacrificial layer;
    shaping the polymer layer, the sacrificial layer, and the planarization layer into a dog-bone-shaped sample;
    etching at least a portion of the sample; and
    drying the sample.

2. The method of claim 1, further comprising forming a copper layer on the polymer layer.

3. The method of claim 1, wherein the forming of the sacrificial layer and the forming of the planarization layer comprises a spin coating method.

4. The method of claim 1, wherein the shaping the polymer layer, the sacrificial layer, and the planarization layer into the sample comprises a press cutting method.

5. The method of claim 4, wherein a length of a gauge of a middle part of the sample is greater than or equal to 4 mm and less than or equal to 6 mm.

6. The method of claim 5, wherein a total thickness of the sample is greater than or equal to 500 nm and less than or equal to 600 nm.

7. The method of claim 1, wherein the drying the sample comprises attaching the sample to an auxiliary guide and air-drying the sample.

8. The method of claim 1, wherein shaping the polymer layer, the sacrificial layer, and the planarization layer into the sample comprises a reactive ion etching (RIE) process utilizing a dog-bone-shaped hard mask.

9. The method of claim 8, wherein a length of a gauge of a middle part of the sample is greater than or equal to 1 mm and less than or equal to 2 mm.

10. The method of claim 9, wherein a total thickness of the sample is greater than or equal to 100 nm and less than or equal to 100 μm.

11. The method of claim 1, wherein shaping the polymer layer, the sacrificial layer, and the planarization layer into the sample comprises a reactive ion etching process after performing a photolithography process utilizing a dog-bone-shaped hard mask.

12. The method of claim 11, wherein a length of a gauge of a middle part of the sample is greater than or equal to 250 μm and less than or equal to 300 μm.

13. The method of claim 12, wherein a total thickness of the sample is greater than or equal to 10 nm and less than or equal to 10 μm.

* * * * *